United States Patent [19]

Suzuki et al.

[11] Patent Number: 5,705,590

[45] Date of Patent: Jan. 6, 1998

[54] WATER ABSORPTION PREVENTING AGENT HAVING WATER SOLUBILITY AND A METHOD FOR PREVENTING WATER ABSORPTION

[75] Inventors: Tomohisa Suzuki; Kenichi Isobe; Mitsuo Asai; Shoji Ichinohe; Akira Yamamoto, all of Matsuida-machi, Japan

[73] Assignee: Shin-Etsu Chem. Co., Ltd., Tokyo, Japan

[21] Appl. No.: 621,682

[22] Filed: Mar. 26, 1996

[30] Foreign Application Priority Data

Mar. 27, 1995 [JP] Japan ..................... 7-093142

[51] Int. Cl.$^6$ .......................................... C08G 77/04
[52] U.S. Cl. ..................... 528/29; 528/14; 528/21; 556/449; 556/463; 556/471; 427/387
[58] Field of Search .................... 556/449, 463, 556/471; 528/29, 14, 21; 427/387

[56] References Cited

U.S. PATENT DOCUMENTS

| | | | |
|---|---|---|---|
| 1,178,731 | 4/1916 | Knorr et al. | 556/449 |
| 4,145,507 | 3/1979 | Wolfers et al. | 556/449 |
| 5,171,476 | 12/1992 | Bloodworth et al. | 556/471 |

*Primary Examiner*—Melvyn I. Marquis
*Attorney, Agent, or Firm*—Townsend & Banta

[57] ABSTRACT

A water soluble water absorption preventing agent mainly comprising an organic silicon compound and/or its partial hydrolytic condensate, represented by the following general formula:

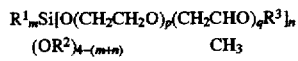

wherein $R^1$ denotes an alkyl group with 1–20 carbon atoms and with a linear chain or branched chain for which a halogen can substitute for part or all of the hydrogen atoms, $R^2$ denotes a hydrogen atom or an alkyl group with 1–10 carbon atoms and with a linear chain or branched chain, $R^3$ denotes a hydrogen atom or an alkyl group with 1–8 carbon atoms and with a linear chain or branched chain, m denotes an integer 1–2 and n denotes an integer 1–3 where m+n=3 or 4, p denotes an integer 1–50, and q denotes an integer 0–25.

6 Claims, No Drawings

WATER ABSORPTION PREVENTING AGENT HAVING WATER SOLUBILITY AND A METHOD FOR PREVENTING WATER ABSORPTION

RELATED APPLICATION

This application claims the priority of Japanese Patent application No. 7-93142 filed on Mar. 27, 1995, which is incorporated herein by reference.

BACKGROUND OF THE INVENTION

1. Field of the Invention

This invention relates to a water absorption preventing agent having water solubility comprising an organic silicon compound and/or its partial hydrolytic condensate, and a method for preventing water absorption in a base material, particularly in a porous material, by applying the water absorption preventing agent.

2. The prior Art

Conventionally known methods for preventing porous construction materials from absorbing water by applying a water absorption preventing agent include a method in which a dissolved resin of silicone, acrylic, urethane, ester or oil/fat or its monomer is applied onto and impregnated into the material and then dried or polymerized.

As the silicone-type water absorption preventing agents, the solvent type and water type are known, of which the solvent type is currently mainly used.

Although the solvent type has superior water absorption preventability, it may cause fire/explosions and poisoning. Therefore, in view of protection of the environment and efficient use of natural resources, it is strongly desired to develop a new water type water absorption preventing agent which does not include a solvent and has superior functionality.

As a water type water absorption preventing agent, an agent of the alkyl silicate type has been used for a long time. However, its water absorption preventability is not sufficient compared with the solvent types, and it has a problem in handling safety because of its strong alkalinity.

Recent examples of the water type water absorption preventing agents include an emulsion prepared by emulsifying alkylalkoxysilane and such in water, disclosed in Japanese unexamined patent publication Tokkai Hei 5-156164 or Tokkai Hei 5-221748. These emulsion type agents constitute the majority of the water type water absorption preventing agents.

They contain silane compounds which have very slow hydrolysis reaction rates, and therefore impregnation goes well when applied on a material. However, silane volatilizes on the surface of the material, and the surface loses water repellency, resulting in water leakage, sticking of stains and popping up due to freezing damage, etc. Such damages may cause a problem in durability and their milky white appearance. Further, its storage stability is limited though adjustment in pH values and such are carried out to stabilize the emulsion, and there are many problems including the complicated process of preparing the emulsion using special equipment.

BRIEF SUMMARY OF THE INVENTION

The object of the invention is to provide a water absorption preventing agent having water solubility, which is easy to use and has semipermanent storage stability, and to provide a method for preventing water absorption in porous materials with a superior water repelling effect.

The present invention is completed by discovering that: by endowing an organic silicon compound with water solubility, the homogeneity at the time of dissolving in water is enhanced and a user only has to dilute the necessary amount in water, and therefore a water absorption preventing agent which is easy to use and has semipermanent storage stability can be provided.

The present invention provides a water absorption preventing agent having water solubility mainly comprising an organic silicon compound and/or its partial hydrolytic condensate, represented by the following general formula:

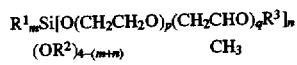

wherein $R^1$ denotes an alkyl group with 1–20 carbon atoms and with a linear chain or branched chain for which a halogen can substitute for part or all of the hydrogen atoms, $R^2$ denotes a hydrogen atom or an alkyl group with 1–10 carbon atoms and with a linear chain or branched chain, $R^3$ denotes a hydrogen atom or an alkyl group with 1–8 carbon atoms and with a linear chain or branched chain, m denotes an integer 1–2 and n denotes an integer 1–3 where m+n=3 or 4, P denotes an integer 1–50, and q denotes an integer 0–25.

Preferably, $R^1$ may be an alkyl group with 3–12 carbon atoms and with a linear chain or branched chain for which a halogen can substitute for part or all of the hydrogen atoms.

The present invention also provides a method for preventing water absorption which comprises the steps of diluting the water absorption preventing agent mentioned above with water, applying or impregnating said diluted water absorption preventing agent onto or into a base material, and heat-drying or rinsing the base material.

Treatment of the base material with an aqueous solution containing a hydrolytic condensation catalyst may be preferably carried out after heat-drying or rinsing.

DETAILED DESCRIPTION

The details of the present invention are described below.

The structure of the organic silicon compound which is the main ingredient of the water absorption preventing agent in the present invention is represented by the following general formula:

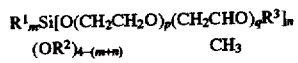

Wherein $R^1$ denotes an alkyl group with 1–20 carbon atoms and with a linear chain or branched chain for which a halogen can substitute for part or all of the hydrogen atoms. Preferably, $R^1$ may be an alkyl group with 3–12 carbon atoms and with a linear chain or branched chain for which a halogen can substitute for part or all of the hydrogen atoms. More preferably, $R^1$ may be a propyl, butyl, pentyl, hexyl, heptyl, octyl, nonyl, decyl, undecyl or dodecyl group.

$R^2$ denotes a hydrogen atom or an alkyl group with 1–10 carbon atoms and with a linear chain or branched chain, and more preferably a hydrogen atom, a methyl, ethyl, propyl or isopropyl group.

$R^3$ denotes a hydrogen atom or an alkyl group with 1–8 carbon atoms and with a linear chain or branched chain, and more preferably a hydrogen atom, a methyl or ethyl group.

m denotes an integer 1–2 and n is an integer 1–3 where m+n=3 or 4. Preferably, m is 1 and n is 2 or 3. Most preferably, m is 1 and n is 3.

p denotes an integer 1-50, preferably an integer 3-50 and more preferably 3-25, and q denotes an integer 0-25, more preferably an integer 0-10.

The organic silicon compound which constitutes the main ingredient of the present invention is composed of at least one of the aforementioned organic silicon compounds and two or more can be used together as well.

The aforementioned organic silicon compounds used in the present invention can be prepared using prior art reactions such as the dehydrochlorination reaction between alkylchlorosilane and polyglycol and the transesterification reaction between alkylalkoxysilane and polygylcol.

Specific examples of the aforementioned organic silicon compounds are shown below.

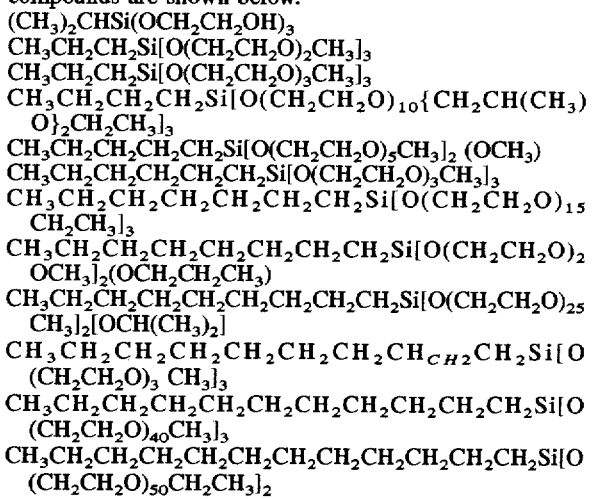

$(CH_3)_2CHSi(OCH_2CH_2OH)_3$
$CH_3CH_2CH_2Si[O(CH_2CH_2O)_2CH_3]_3$
$CH_3CH_2CH_2Si[O(CH_2CH_2O)_3CH_3]_3$
$CH_3CH_2CH_2CH_2Si[O(CH_2CH_2O)_{10}\{CH_2CH(CH_3)O\}_2CH_2CH_3]_3$
$CH_3CH_2CH_2CH_2CH_2Si[O(CH_2CH_2O)_5CH_3]_2(OCH_3)$
$CH_3CH_2CH_2CH_2CH_2CH_2Si[O(CH_2CH_2O)_3CH_3]_3$
$CH_3CH_2CH_2CH_2CH_2CH_2CH_2Si[O(CH_2CH_2O)_{15}CH_2CH_3]_3$
$CH_3CH_2CH_2CH_2CH_2CH_2CH_2CH_2Si[O(CH_2CH_2O)_2OCH_3]_2(OCH_2CH_3)$
$CH_3CH_2CH_2CH_2CH_2CH_2CH_2CH_2CH_2Si[O(CH_2CH_2O)_{25}CH_3]_2[OCH(CH_3)_2]$
$CH_3CH_2CH_2CH_2CH_2CH_2CH_2CH_{CH2}CH_2Si[O(CH_2CH_2O)_3CH_3]_3$
$CH_3CH_2CH_2CH_2CH_2CH_2CH_2CH_2CH_2CH_2Si[O(CH_2CH_2O)_{40}CH_3]_3$
$CH_3CH_2CH_2CH_2CH_2CH_2CH_2CH_2CH_2CH_2CH_2Si[O(CH_2CH_2O)_{50}CH_2CH_3]_2$

Of these compounds, the most preferable are the organic silicon compounds whose structure have 3 polyether groups.

Also, a partial hydrolytic condensate which is the aforementioned organic silicon compound partially hydrolyzed in water can be used for the organic silicon compound for the water absorption preventing agent of the present invention.

When using the water absorption preventing agent of the present invention, the aforementioned organic silicon compound and/or its partial hydrolytic condensate is diluted with water generally to a concentration of 1-40 wt %, preferably 5-30 wt %. It is not preferable to dilute the organic silicon compound and/or its partial hydrolytic condensate too much, because the water absorption preventing agent cannot exhibit satisfactory performance and the necessary amount of the water absorption preventing agent to be applied becomes large, leading to a longer drying time. On the other hand, if the concentration of organic silicon compound and/or its partial hydrolytic condensate is 40 wt % or more, then the dilution becomes insufficient and the resulting too high concentration may cause phase separation, and the high viscosity causes poor permeation which may lead to spottiness in coating.

A catalyst which accelerates hydrolysis, alcohol and such which improves water solubility and organic acid and such which maintains stability of the aqueous solution can be added to the water absorption preventing agent as necessary when diluting in water.

An antiseptic agent, a mildewproof agent and an antproof agent, as well as CMC (carboxymethyl cellulose), PVA (polyvinyl alcohol), water soluble acrylic resin, SBR (styrene-butadiene rubber) latex, colloidal silica, etc. can be added as secondary additives to the water absorption preventing agent.

Examples of the base material onto which the water absorption preventing agent can be applied include porous materials, lumber, natural fibers, synthetic fibers and inorganic fibers, of which porous materials are particularly preferable. Examples of the porous materials include materials mainly composed of inorganic materials, light-weight concrete, precast concrete, light-weight foaming concrete or autoclaved light-weight concrete (ALC), mortar, joint mortar, cemented asbestos boards, cemented pulp boards, cemented excelsior boards, glass fiber reinforced cement (GRC) boards, carbon fiber reinforced cement boards, calcium silicate boards, gypsum boards, hard boards, dolomite plaster, blocks, bricks, tiles, roof tiles, natural stones, glass wool, rock wool and ceramic fibers.

The method for preventing water absorption according to the present invention comprises the steps of diluting the water absorption preventing agent with water, applying or impregnating the diluted water absorption preventing agent onto or into a base material, and heat-drying or rinsing the base material. Treatment of the base material with an aqueous solution containing a hydrolytic condensation catalyst may follow after heat-drying or rinsing if necessary.

The water absorption preventing agent of the present invention impregnated or applied onto or into the base material forms a firm and excellent water repellant layer or water absorption preventing layer by a hydrolysis reaction and a condensation reaction. However, polyglycol produced by the hydrolysis reaction does not volatilize but rather adheres to the surface of the water repellant layer. Polyglycol increases hydrophilicity in the base material and, its natural water repellency is not realized. Therefore, heat-drying or water rinsing of the base material is carried out to remove the polyglycol.

The heat-drying is conducted at 80°-250° C. for 3-48 hours, preferably at 100°-200° C. for 6-36 hours. It is not preferable if the temperature is lower than 80° C. or the duration is shorter than 3 hours because polyglycol is hard to volatilize. On the other hand, it is not preferable if the temperature is higher than 250° C. or the duration is longer than 48 hours, because the siloxane bonding of the organic silicon compound of the water absorption preventing agent is severed.

Water rinsing of the base material can be carried out by making the base material contact with water such as by soaking or rinsing off. Practically, it is enough to simply apply said water absorption preventing agent, diluted with water, on the base material and leave it outdoors, because exposure to rain water can achieve water rinsing and thus water repellency will be manifested.

When the porous inorganic materials mentioned above, particularly bricks, tiles, roof tiles, natural stone, glass wool, rock wool, ceramic fiber, etc., are neutral, it is preferable to dilute the water soluble water absorption preventing agent of the present invention, apply or impregnate it onto or into the base material and treat it with an aqueous solution which contains a hydrolytic condensation accelerator catalyst.

Examples of the hydrolytic condensation accelerator catalyst include alkaline substances including hydroxides of alkali or alkali earth metals, amine compounds and alkali silicates, acidic substances including inorganic acids including hydrochloric acid and nitric acid, organic acids including sulfonic acid and maleic acid, fluorine compounds which generate fluorine ions in water, such as KF and tetrabutylammonium fluoride. An aqueous solution of one of them is prepared and the base material is soaked in it for the treatment. The concentration of the aqueous solution is 0.01-3%, preferably 0-1-1%. The pH of the aqueous solution for the alkaline conditions should preferably be adjusted to around 10. If the pH is 11 or higher, then efflorescence of the base material will be accelerated. If the pH is 9 or lower, then the hydrolytic condensation rate may become too low to obtain the effect. For the acidic conditions, the pH should preferably be adjusted to around 4. If the pH is 3 or lower, then durability of the base material will be reduced. If the pH is 5 or higher, then the catalytic effect may not be obtained.

As described thus far, the water absorption preventing agent having water solubility of the present invention not only can help solving various problems of porous materials due to water, such as rain water leakage, deterioration of the material caused by acid rain, stain absorption, salt damage caused by sea water, freezing damage in cold areas and efflorescence caused by elution of the salts in the material, but is a superior waterproofed primer for various paints and finishing materials. Further, the water absorption preventing agent having water solubility of the present invention is easy to use and has superior storage stability.

EXAMPLES

The present invention is described below by referring to examples, however, the present invention is not limited to the following examples.

Preparation Example 1

Tris (methyltriglycoloxy) propylsilane $CH_3CH_2CH_2Si[O(CH_2CH_2O)_3CH_3]_3$ 80 g (0.45 mol) of propyltrichlorosilane was put into a 500 ml four neck flask equipped with a cooling pipe, a thermometer and a dripping funnel, followed by stirring. After raising the inside temperature up to 100° C., 148 g (0.90 mol) of methyltriglycol was dripped into it and, as a result, the temperature in the flask dropped down to 80° C. After 1 hour of stirring at 100° C., 111 g (0.68 mol) of methyltriglycol and 40.6 g (0.68 mol) of urea were added, followed by 2 hours of aging at 100° C. After the aging, the reaction mixture was separated to remove ureahydrochloride and the product thus obtained was neutralized with 0.6 g of propylene oxide. After neutralization, the floating ureahydrochloride was removed using 1.0 g of activated carbon and, after filtering and stripping, 240.6 g of colorless transparent liquid was obtained. This liquid was analyzed using $^1$H-NMR spectroscopy and confirmed to be the aforementioned compound.

Preparation Example 2

Tris (methyltriglycoloxy) hexylsilane $CH_3(CH_2)_5Si[O(CH_2CH_2O)_3CH_3]_3$

The aforementioned compound was obtained in the same manner as Preparation example 1 except for the fact that hexyltrichlorosilane was used instead of propyltrichlrosilane.

Preparation Example 3

Tris (methyltriglycoloxy) decylsilane $CH_3(CH_2)_9Si[O(CH_2CH_2O)_3CH_3]_3$ 92 g (0.35 mol) of decyltrimethoxysilane, 213 g (1.3 mol) of methyltriglycol and 0.1 g of KOH were put into a 500-ml four neck flask equipped with a cooling pipe, a thermometer and a dripping funnel, followed by stirring. After gradually raising the inside temperature up to 150° C., 10 hours of aging was done. The mixture was then cooled and 0.2 g of synthetic adsorbent ("KYOWADO 600" from KYOWAKAGAKU KOGYO) and 1 g of activated carbon was added, followed by 2 hours of stirring. Filtering and stripping of this produced 227 g of colorless transparent liquid. This liquid was analyzed using $^1$H-NMR spectroscopy and confirmed to be the aforementioned compound.

Example 1

20 parts of the water absorption preventing agent obtained in Preparation example 1 was diluted with 80 parts of water and was used to soak and cure mortar, and then baked for 24 hours at 150° C. for heat-drying to prepare an evaluation sample. This sample was tested for the surface conditions, water absorption prevention performance, permeation depth and water repellency. The results are shown in Table 1.

(a) Surface conditions and water absorption prevention performance (water absorption ratio)

The whole surface of a JIS mortar (50×50×25 mm) was soaked with a water dilution of the water absorption preventing agent for 5 minutes such that the concentration of the active ingredient would be 100 g/m$^2$. After curing for 7 days at 25° C. and 50% RH, it was baked at 150° C. for 24 hours. The surface condition was visually observed. The evaluation criteria are listed below.

Evaluation criteria for the surface condition
○: No wet color observed
x: Wet color observed The whole surface of this specimen was then soaked in tap water for 28 days and the water absorption ratio was calculated using the following equation to measure the water absorption prevention performance.

Water absorption ratio (%)={(weight of mortar after water absorption)−(weight of mortar before treatment)}/(weight of mortar before treatment)×100

(b) Permeation depth

A specimen which had been soaked/cured/baked in the same manner as in the aforementioned (a) test was longitudinally cut in half, and water was applied on a cross section to facilitate observation of the hardened layer. The permeation depth from the surface (in "mm" units) was measured.

Permeation depth is an index of a depth of a water repellent layer and is not an index of water repellency.

(c) Water repellency 0.5 cc of water was dripped onto the surface of a specimen which had been soaked/cured/baked in the same manner as in the aforementioned (a) test, and the condition of the surface was visually observed. The evaluation criteria are listed below.

Evaluation criteria
○: Large contact angle (adequate water repellency)
Δ: Medium contact angle
x: Water absorption occurs.

Example 2

Using the water absorption preventing agent obtained in Preparation example 2, various performance tests were conducted in the same manner as in Example 1. The results are shown in Table 1.

Example 3

Using the water absorption preventing agent obtained in Preparation example 3, various performance tests were conducted in the same manner as in Example 1. The results are shown in Table 1.

Example 4

The water absorption preventing agent obtained in Preparation example 1 was used to soak and cure mortar and then, after soaking in tap water for 24 hours, 24 hours of drying was done at 25° C. and 50% RH to prepare the evaluation sample. This sample was tested for (a) the surface conditions and the water absorption prevention performance (water absorption ratio), (b) permeation depth and (c) water repellency.

The results are shown in Table 1.

Example 5

Using the water absorption preventing agent obtained in Preparation example 2, various performance tests were conducted in the same manner as in Example 4. The results are shown in Table 1.

Example 6

Using the water absorption preventing agent obtained in Preparation example 3, various performance tests were conducted in the same manner as in Example 4. The results are shown in Table 1.

Comparative Example 1

The results of the performance tests for mortar which had not been treated with the aforementioned water absorption preventing agent for porous materials are shown in Table 1.

Comparative Example 2

100 parts of alkyl silicate type water soluble water absorption preventing agent Polon C (a product from Shin-Etsu Chemical Co., Ltd. with a silicon content of 20%, usually used by impregnating it into the base material) was used to soak and cure mortar to prepare an evaluation sample. Various performance tests were conducted on this sample in the same manner as in Example 1. The results are shown in Table 1.

TABLE 1

| | Surface condition | Water absorption ratio (wt %) | Permeation depth (mm) | Water repellency |
|---|---|---|---|---|
| Example 1 | ○ | 1.7 | 2.5 | ○ |
| Example 2 | ○ | 1.3 | 2.5 | ○ |
| Example 3 | ○ | 1.8 | 3.0 | ○ |
| Example 4 | ○ | 1.2 | 3.0 | ○ |
| Example 5 | ○ | 0.6 | 2.5 | ○ |
| Example 6 | ○ | 0.9 | 2.5 | ○ |
| Comparative example 1 | ○ | 7.2 | 0 | x |
| Comparative example 2 | ○ | 3.1 | 1.0 | Δ |

Preparation Example 4

Tris (methyltriglycoloxy) decylsilane $CH_3(CH_2)_9Si[O(CH_2CH_2O)_3CH_3]_3$ 92 g (0.35 mol) of decyltrichlorosilane was put into a 500 ml four neck flask equipped with a cooling pipe, a thermometer and a dripping funnel, followed by stirring. After raising the inside temperature up to 100° C., 147.6 g (0.9 mol) of methyltriglycol was dripped into it and, as a result, the temperature in the flask dropped down to 80° C. After 1 hour of stirring at 100° C., 110.7 g (0.68 mol) of methyltriglycol and 40.6 g (0.68 mol) of urea were added, followed by 2 hours of aging at 100° C. After the aging, the reaction mixture was separated to remove ureahydrochloride and the product thus obtained was neutralized with 0.6 g of propylene oxide. After neutralization, the floating ureahydrochloride was removed using 1.0 g of activated carbon and, after filtering and stripping, 619.4 g of a colorless transparent liquid was obtained. This liquid was analyzed using $^1$H-NMR spectroscopy and confirmed to be the aforementioned compound.

Example 7

20 parts of the water absorption preventing agent obtained in Preparation example 4 was diluted with 80 parts of water and used to soak and cure a brick(s) (from NIPPON RENGA). The bricks were then soaked in an aqueous solution of 1% maleic acid for 24 hours and dried for 24 hours to prepare an evaluation sample(s). This sample was tested for the surface conditions, water absorption prevention performance, permeation depth and water repellency. The results are shown in Table 2.

(a) Surface conditions and water absorption prevention performance (water absorption ratio)

The whole surface of a brick (210×100×30 mm) was soaked with a water dilution of the water absorption preventing agent for 5 minutes such that the concentration of the active ingredient would be 100 g/m². After curing for 7 days at 25° C. and 50% RH, it was soaked in a 1% aqueous solution of maleic acid for 24 hours and dried for 24 hours at 25° C. and 50% RH. The surface condition was visually observed. The evaluation criteria are listed below.

Evaluation criteria for the surface condition

○: No wet color observed
x: Wet color observed

The whole surface of this specimen was then soaked in tap water for 28 days and the water absorption ratio was calculated using the following equation to measure the water absorption prevention performance.

Water absorption ratio (%)={(weight of brick after water absorption)−(weight of brick before treatment)}/(weight of brick before treatment)×100

(b) Permeation depth

A specimen which had been soaked/cured/baked in the same manner as in the aforementioned (a) test was longitudinally cut in half, and water was applied on the cross section to facilitate observation of the hardened layer. The permeation depth from the surface (in "mm" units) was measured.

(c) Water repellency 0.5 cc of water was dripped onto the surface of a specimen which had been soaked/cured/baked in the same manner as in the aforementioned (a) test, and the surface condition was visually observed. The evaluation criteria are listed below.

Evaluation criteria

○: Large contact angle (adequate water repellency)
Δ: Medium contact angle
x: Water absorption occurs.

Example 8

Various performance tests were conducted in the same manner as in Example 7 except for the fact that a 1% aqueous solution of KF was used instead of the 1% aqueous solution of maleic acid used in Example 7. The results are shown in Table 2.

Example 9

Various performance tests were conducted in the same manner as in Example 7 except for the fact that a 1% aqueous solution of the reaction product of methylsilsesquioxane and sodium was used instead of the 1% aqueous solution of maleic acid used in Example 7. The results are shown in Table 2.

Comparative Example 3

The results of the various performance tests on a brick(s) which had not been treated with the aforementioned water absorption preventing agent for porous materials are shown in Table 2.

TABLE 2

| | Surface condition | Water absorption ratio (wt %) | Permeation depth (mm) | Water repellency |
|---|---|---|---|---|
| Example 7 | ○ | 0.4 | 4.0 | ○ |
| Example 8 | ○ | 0.3 | 5.0 | ○ |
| Example 9 | ○ | 0.1 | Permeated all the way | ○ |
| Comparative example 3 | ○ | 10.3 | 0 | x |

What is claimed is:

1. A water soluble absorption preventing agent having water solubility comprising an organic silicone compound and/or its partial hydrolytic condensate, represented by the following general formula:

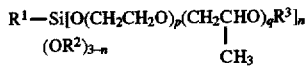

wherein $R^1$ denotes a linear chain or branched chain alkyl group having 1–20 carbon atoms for which a halogen can be substituted for part or all of the hydrogen atoms;

$R^2$ denotes a hydrogen atom or a linear chain or branched chain alkyl group having 1–10 carbon atoms;

$R^3$ denotes a hydrogen atom or a linear chain or branched chain alkyl group having 1–8 carbon atoms;

n denotes 2 or 3;

p denotes an integer 1–50; and q denotes an integer 0–25.

2. A water soluble water absorption preventing agent having water solubility of claim 1, wherein n is 3.

3. A water soluble water absorption preventing agent having water solubility of claim 1, wherein $R^1$ is a linear chain or branched chain alkyl group having 3–12 carbon atoms for which a halogen can be substituted for part or all of the hydrogen atoms;

$R^2$ is selected from a hydrogen atom, methyl, ethyl, propyl or isopropyl group; and $R^3$ is selected from a hydrogen atom, a methyl or ethyl group.

4. A method for preventing water absorption comprising the steps of:

applying to a substrate a water soluble water absorption preventing agent having water solubility comprising an organic silicon compound and/or its partial hydrolytic condensate, represented by the following formula:

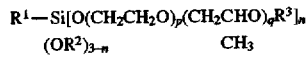

wherein $R^1$ denotes the linear chain or branched chain alkyl group having 1–20 carbon atoms for which a halogen can substitute for part or all of the hydrogen atoms;

$R^2$ denotes a hydrogen atom or a linear chain or branched chain alkyl group having 1–10 carbon atoms;

$R^3$ denotes a hydrogen atom or linear chain or branched chain alkyl group having 1–8 carbon atoms;

n denotes 2 or 3;

p denotes an integer 1–50; and q denotes an integer 0–25.

5. The method for preventing water absorption of claim 4, further comprising heat drying or rinsing said substrate treated with said soluble water absorption preventing agent, and then treating said substrate with an aqueous solution containing a hydrolytic condensation catalyst.

6. The method for preventing water absorption of claim 4, wherein said substrate is a porous material.

* * * * *